United States Patent [19]

Luddy

[11] Patent Number: 4,971,904

[45] Date of Patent: Nov. 20, 1990

[54] HETEROGENEOUS IMMUNOASSAY

[75] Inventor: Michael A. G. Luddy, Poughquag, N.Y.

[73] Assignee: E. I. Du Pont de Nemours and Company, Wilmington, Del.

[21] Appl. No.: 150,291

[22] Filed: Jan. 29, 1988

Related U.S. Application Data

[63] Continuation-in-part of Ser. No. 66,583, Jun. 26, 1987, abandoned.

[51] Int. Cl.$^5$ .................. G01N 33/53; G01N 33/543; C12N 11/00
[52] U.S. Cl. ........................................ 435/7; 435/174; 436/501; 436/518; 436/538; 436/823; 436/825; 530/810
[58] Field of Search ................... 435/7, 174, 176, 177; 436/501, 518, 524, 527, 528, 529, 530, 536, 823, 825; 530/811, 812, 810

[56] References Cited

U.S. PATENT DOCUMENTS

| | | | |
|---|---|---|---|
| 3,654,090 | 4/1972 | Schuurs et al. | 195/103.5 |
| 4,098,876 | 7/1978 | Piasio et al. | 424/1 |
| 4,200,436 | 4/1980 | Mochida et al. | 23/230 B |
| 4,298,687 | 11/1981 | Maes | 435/7 |
| 4,376,110 | 3/1983 | David et al. | 436/513 |
| 4,482,636 | 11/1984 | Mochida et al. | 436/518 |
| 4,654,299 | 3/1987 | Lentfer | 435/7 |

FOREIGN PATENT DOCUMENTS 1020866  1/1986  Japan .................. 436/518

OTHER PUBLICATIONS

Oellerich, J. Clin. Chem. Clin. Biochem., vol. 22, 1984, pp. 895–904.
Yolken, Reviews of Infectious Diseases, vol. 4(1), 1982, pp. 35–68.
Tijssen, Laboratory Techniques in Biochemistry and Molecular Biology, vol. 15, Editors Burdon et al., 1985, pp. 297–305.

Primary Examiner—Esther L. Kepplinger
Assistant Examiner—Florina G. Hoffer
Attorney, Agent, or Firm—George A. Frank

[57] ABSTRACT

An improved heterogeneous immunoassay is provided which includes the utilization of support materials capable of reversible immobilization of proteinaceous binding partners of biological material of interest and the removal of labeled complexes from these supports through the use of release reagents permitting the subsequent solution phase determination of the amount of label.

4 Claims, No Drawings

HETEROGENEOUS IMMUNOASSAY

REFERENCE TO RELATED APPLICATION

This application is a continuation-in-part of application Ser. No. 066,583 filed June 26, 1987, now abandoned.

TECHNICAL FIELD

This invention relates to heterogeneous immunoassays and, more specifically, to heterogeneous immunoassays which measure the amount of the bound phase complex after the release of such a complex from the immobilizing support.

BACKGROUND ART

In recent years a number of immunoassay techniques has been developed for the measurement of clinically important ligands. Typically, a competitive binding immunoassay utilizes a conjugate of a labeling substance and a binding component which participates in a binding reaction to produce two species of labeled complexes a bound species and a free species. The relative amounts of the labeled complexes are a function of the amount of the ligand to be detected in the test sample.

Where the labeling substance in the bound species and in the free species are substantially indistinguishable by the means used to measure the labeling substance, the bound and the free species must be physically separated. This type of assay is referred to as heterogeneous.

The two most widely used heterogeneous immunoassays are the radioimmunoassay (RIA) and the enzyme linked immunosorbant assay (ELISA). In the RIA, a sample containing an unknown amount of antigen is mixed with a known amount of radiolabeled antigen and antibody. The assay components are allowed to react to near-equilibrium and then the antibodY-bound antigen is separated from the unbound antigen. Since sample antigen competes with the labeled antigen for a limited number of antibody binding sites the more antigen in the sample the less labeled antigen is in the bound fraction (or the more is in the unbound fraction). This type of assay is generally time-consuming (1-3 hours) and labor intensive.

RIA suffers from two major disadvantages: First, the labeling substance employed is a radioisotope which poses numerous problems associated with handling storage and disposal. Second, RIA is performed in a competitive mode (i.e.. the analyte and the labeled analyte compete for a limited number of binding sites on the antibody), and, therefore, the antibody affinity constant limits the sensitivity of the assay, typically in the range of $10^{-8}M^{-1}$ to $10^{-11}M^{-1}$.

ELISA is similar in principle to RIA except that the labeling substance is an enzyme rather than a radioisotope. It still suffers from the limitation that sensitivity is a strict function of the antibody affinity constant.

Other labeling substances have been described in addition to isotopes and enzymes. These include fluorophores, coenzymes bioluminescent materials and enzyme inhibitors.

Various methods of effecting the separation step in heterogeneous immunoassays are known. These include filtration, centrifugation and chromatography.

The use of affinity columns to effect the separation step has been described in French Patent Appl. No. 79 15992, published Jan. 9, 1981. It describes the use of a gel having coupled to it a ligand which has affinity for the labeling substance and which additionally has molecular sieving properties. The use of a gel having affinity for the ligand of interest rather than for the labeling substance and having molecular sieving properties is also disclosed. The assay described can be performed in a competitive or noncompetitive mode.

U.S. Pat. No. 4,298,687, issued Nov. 3, 1981 to Maes, discloses a heterogeneous immunoassay in which the substance to he determined is reacted with a labeled primary binding partner and the unreacted binding partner is then captured by absorption on a solid phase endowed with specific binding properties for the primary binding partner. The bound primary binding partner is then measured by reacting a labeled binding partner specific for the primary binding partner with the bound primary binding partner. The label is measured while still bound to the solid support. Since the primary binding partner is present in a limited amount, the reaction kinetics and equilibrium are adversely affected.

U.S. Pat. No. 3,654,090, issued April 4, 1972 to Schuurs et al., describes a noncompetitive heterogeneous immunoassay for human chorionic gonadotropin (HCG) which uses an excess of enzyme-labeled divalent antibody and an immobilized HCG column to accomplish the separation step.

U.S. Pat. No. 4.200,436, issued April 29, 1980, to Mochida et al. discloses an immunoassay employing a labeled monovalent antibody in which immobilized antigen (the same antigen as that to be measured) is used to separate the free labeled antibody from the labeled antibody-antigen complex. Since it is primarily the bound fraction which is measured this assay is usually performed in a competitive mode. Hence, sensitivity is limited by the affinity constant of the antibody when the assay is performed according to the preferred mode.

U.S. Pat. No. 4,098,876, issued July 4, 1978, to Piasio et al., discloses a reverse sandwich immunoassay in which the analyte is incubated with labeled antibody prior to incubating with the immobilized second antibody. After separation of the bound, labeled complex from the incubation medium, the bound label is measured.

U.S. Pat. No. 4,376,110, issued March 8, 1983, to David et al., discloses the use of monoclonal antibodies in a two-site sandwich immunoassay format. The preferred mode disclosed involves the measurement of the bound label after separation from the free label.

The preferred mode of operation of the heterogeneous immunoassay techniques described above is to utilize excess primary labeled binding partners and/or excess bound secondary binding partners to enhance the speed, sensitivity and precision of the assay. When operating in this preferred mode, it becomes necessary to measure the activity of the bound label since there is generally too much free label to allow accurate detections of the small decrease in the amount of free label. The detection of bound label is particularly difficult in some automated analyzers where it is often necessary to introduce the sample to the analyzer in a liquid form.

Materials such as proteins, protein-hapten conjugates and specifically antibodies can be adsorbed onto the surface of solid or liquid supports, such as polyethylene, polycarbonates, perfluorocarbon polymers, latex particles glass and magnetic particles with polystyrene being preferred. In general this adsorption is considered to be irreversible even in the presence of surfactants chaotropes, denaturants such as 8M urea or guanidine hydrochloride. [Methods in Enzymology, XL, 149, Ed. K. Mosbach, Academic Press (1976); Morrissey, B. W. Annals of the New York Academy of Sciences, 283, 50-64 (1977)].

While proteins are thought to be irreversibly bound under many aqueous conditions some solvents may cause desorption from hydrophobic surfaces. For example, dimethylsulfoxide (DMO) and tetrahydrofuran (THF) have been used in hydrophobic chromatography to desorb proteins that were adsorbed from aqueous solution onto hydrophobic supports. Presumably by changing the van der Waals or London forces between the protein and the support. These solvents, however, often attack and dissolve organic supports and. at least in the case of DMSO, denature many proteins such as enzymes. [J. Colloid and Interface Science Vol. 76, No. 1, 254-255 (1980); C. J. Van Oss et al.. Sep. Purif. Methods, Volume 7, 245 (1978); C. J. van Oss et al. Sep. Sci. Technol., Volume 14, 305 (1979)].

There exists a need for an improvement in the heterogeneous immunoassay art which has all of the advantages of the known heterogeneous immunoassay techniques but which allows rapid detection of the bound label in common automated analyzer systems.

DISCLOSURE OF INVENTION

The improved heterogeneous immunoassay of this invention comprises any standard heterogeneous immunoassay wherein the improvement comprises the modification of assay steps as follows:
(a) adsorbing a binding partner of the analyte of interest on a solid or liquid support to permit subsequent release of said binding partner from said support after the formation of a first complex between the binding partner and said analyte;
(b) storing said support having said binding partner adsorbed thereon under conditions which preserve said releasability;
(c) contacting the second complex formed between said first complex and a labeled binding partner with a release agent selected from the group consisting of monovalent salts, surfactants and organic bases; and
(d) measuring the amount of label in said second complex released in step (c) from said support.

DESCRIPTION OF INVENTION

In general, the immunoassay of this invention can be used with any of the currently known heterogeneous immunoassay techniques in which it is desirable to measure the amount of label in the immobilized phase. These include the standard ELISA, sandwich, and reverse sandwich assay techniques. The only requirement is that the binding partner such as an antibody which is immobilized on the solid or liquid immobilizing phase be reversibly bound to it. The instant invention can be used with a variety of binding partners and will be exemplified through the use of antibodies. AnY antibody such as polyclonal, monoclonal, whole and fragmented antibodies can be used.

In the event the coated immobilizing support is not utilized within a short time period after its preparation, approximately 1 hour, the support bearing the immobilized binding partner needs to be kept in contact with a phosphate buffered saline optionally containing BSA. The BSA content can range from 0.05-30%. If the solid phase is allowed to dry out, the immobilized binding partner will not completely release (desorb) in the presence of the release reagents of the invention. BSA functions to increase long-term stability of the proteins immobilized on the support. It is expected that other proteins can function similary to BSA.

The adsorption of proteins or other macromolecules useful as immobilized binding partners in heterogeneous immunoassays to supports described above must be carried out in a way that permits the later release of the complex formed during the assay from the support. Conditions necessary to achieve this reversible adsorption can vary for different binding partners and is a matter of known optimization techniques. A critical parameter controlling reversible adsorption of binding partner is the length of time the solution of the binding partner is in contact with the support. Generally, times of 60 min. or less are preferred with 15-30 min. being most preferred. If the adsorption time is too short there will be too little immobilized binding partner to give adequate assay sensitivity. If the adsorption time is too long the adsorption becomes irreversible.

A second parameter which is important in attaining reversible adsorption is the adsorption milieu. Assay mixtures which can denature or partially denature the binding partner should be avoided. This includes the use of extremes of pH or salt concentrations. A preferred milieu is phosphate buffered saline (120 mM sodium chloride, 2.7 mM potassium chloride, 10 mM phosphates, pH 6.0). Additionally, the temperature of adsorption also needs to be regulated to prevent denaturation of the binding partner; temperatures in the range of 20°-25° C. are preferred.

After the binding partner has been adsorbed onto the support, the remaining adsorption sites on the support can be blocked using common blocking agents such as bovine serum albumin in PBS at pH 7.5. This reduces the amount of binding partner which can become irreversibly adsorbed and also reduces the amount of nonspecific binding in the immunoassay.

Any suitable materials can serve as a support for reversible immobilization of the proteins used for the capture of the biological material of interest. The immobilizing supports can be solid or liquid and include polystyrenes, polyethylenes, polycarbonates, perfluorocarbon polymers, glass, coated magnetic particles and a variety of latex particles. The support is not only capable of carrying the protein binding partner of the biological material of interest but also the complex formed between the binding partner and the material of interest (often referred to as the analyte) and any further complexes (often taking the form of a double complex referred to as a "sandwich"). collectively referred to as the complex. When treated with the release reagent of this invention, the immobilized complex is removed from the support permitting the subsequent liquid phase determination of the label present on one of the members of the complex.

The desorption of proteins or other macromolecules useful as immobilized binding partners in heterogeneous immunoassays and their complexes can be achieved through the use of release reagents. The release reagents of this invention are high ionic strength solutions and include monovalent salts such as sodium chloride organic bases such as 2-amino-2-methyl-1-propanol, trishydroxymethylaminomethane and, preferably, diethanolamine (DEA), ionic and non-ionic surfactants, such as sodium dodecyl sulfate (SDS). alkylaryl polyether alcohol and polyoxyethylene sorbitan monolaurate and combinations of salts, organic bases and/or surfactants. The selection of release reagent is concentration dependent; high concentrations of any of the above or lower concentrations of combinations of the above can suffice. Minimum levels can be determined functionally. At low, buffer-type concentrations, the salts and organic bases do not act as release reagents.

The preferred composition of the release reagent is 1.0M DEA, 0.1 mM $MgCl_2$, and 0.5% Tween 20, pH 8.9, although a wide range of pH, $Mg^{+2}$, and Tween 20 concentrations are effective.

The exact composition of the release reagent has to be selected to be compatible with the label of the binding partner while also being effective for the release of the complex from the solid support. For example, if acid is a denaturant for the label then a neutral or basic release reagent should be used. For example, when the label is alkaline phosphatase, a pH of 8.9 is preferred and when the label is $\beta$-galactosidase a pH of 7.6 is preferred.

Any detectable label conjugated to a second binding partner of the analyte can function in the immunoassay of this invention. These include enzymes, radioisotopes, luminescent materials, fluorophores, coenzymes enzyme inhibitors and enzymes. The latter are preferred.

The assay of this invention can be performed as follows: A solid support, usually a polystyrene tube (10×75 mm), is coated at room temperature using PBS (phosphate buffered saline), pH 6.0, containing 10 micrograms per mL of the binding partner of interest, usually an antibody. After approximately 30 min. of incubation. the tube is washed three times with PBS containing 0.1% bovine serum albumin, pH 7.6. Finally, the coated tube is filled with PBS containing 0.1% BSA pH 7.6. This solution is discarded before the start of the immunoassay procedure. After decanting, a known volume of patient sample, usually 500 µL of serum containing an unknown amount of analyte, is mixed with 500 µL of an anti analyte-label conjugate in the coated polystyrene tube. The tube is capped and rotated end-over-end at 30 r.p.m. for 15 min at 37° C.. After rotating, the bound labeled complex so formed is washed three times with deionized water. The complex sandwich is released from the surface of the tube by adding 800 µL of the release reagent to the tube and rotating end-over-end at 30 r.p.m. for 5 min. at 37° C. The activity of the label in the resulting solution the so-called release solution, can now be measured.

The assay of this invention can be performed manually or it can be adapted to a variety of automated or semi-automated instrumentation such as the aca ® discrete clinical analyzer (a registered trademark of by E. I. du Pont de Nemours & Company, Wilmington, DE). Using an aca ® analyzer, all steps through the release of the complex from the tube wall are performed outside of the instrument. A known volume of the release solution is automatically injected into an analytical test pack (described in U.S. Pat. No. Re. 29,725 to Johnson et al. reissued Aug. 8, 1978, incorporated herein by reference) in the filling station of the instrument, followed by a volume of buffer sufficient to bring the final in-pack volume to 5 mL. The pack is automatically processed at 37° C. with addition of reagents required for the signal generating reaction at either breaker/mixer I or breaker/mixer II and photometric readout of the signal.

The assay of this invention can be performed manually as follows. A portion of the release reagent is added to 0.75 mL of release reagent containing 1 mM para-nitrohenyl phosphate and incubated for 15 minutes at 37° C.. A blank is also run. After the incubation, the reaction is quenched with 0.75 mL of 0.15M phosphate buffer, pH 7.8. The quenched reaction is read at 405 nanometers on a spectrophotometer, such as the Hybritech photon ERA.

EXAMPLE 1

Polystyrene tubes (Falcon 12×75 mm) were coated with 0.2 mL of rabbit anti-ferritin antibody (Dako #082, rabbit, IgG fraction, 0.1 mg/mL) diluted in phosphate buffered saline (Sigma Chemical P8033, 120 mM sodium chloride, 2.7 mM Potassium chloride and 10 mM phosphates pH 7.6). After 15 minutes, the tubes were aspirated washed three times with 1 mL of water and aspirated again. To each tube was added 0.1 mL of sample containing an unknown amount of ferritin or calibrator.(containing a known amount of ferritin) and 0.05 mL of enzyme-antibody conjugate (anti-ferritin-alkaline phosphatase conjugate Hybritech Inc., San Diego CA). After incubating for 15 minutes at 37°, the reaction was stopped and the solution was decanted. After decanting, the tubes were washed three times with 5 mL of deionized water. The tubes were drained, 0.2 mL of Release Reagent A (1.0M DEA, 0.1 mM $MgCl_2$, pH 8.9) was added and incubated for 15 minutes at 37°. A 0.12-mL aliquot was removed and transferred to a second tube (uncoated) containing 0.75 mL of Release Reagent A containing 1 mM para-nitrophenylphosphate. After incubating for 15 minutes at 37 degrees, the reaction was stopped by the addition of 0.75 mL of phosphate buffer (0.15M, pH 7.8). The hydrolysis of the para-nitrophenylphosphate was measured at 405 nanometers on a commercially available spectrophotometer (Photon ERA Spectrophotomer, Hybritech). A dose curve was constructed from the data, obtained with the calibrators shown in Table 1.

TABLE 1

| Ferritin Concentration | Absorbance at 405 nm |
| --- | --- |
| 0 nanogram/mL | 0.045 |
| 50 nanogram/mL | 0.122 |
| 100 nanogram/mL | 0.223 |
| 250 nanogram/mL | 0.458 |
| 500 nanogram/mL | 0.482 |

EXAMPLE 2

Sample cups utilized with the aca ® analyzer were coated with 1.0 mL of rabbit anti-ferritin antibody (Dako #082B, rabbit IgG fraction) diluted in phosphate buffered saline (Sigma Chemicals P8033, 120 mM sodium chloride. 2.7 mM potassium chloride and 10 mM phosphates pH 7.6.) After rocking the sample cups on an Ames Rocker for 30 minutes at room temperature, the sample cups were drained and washed three times with 5.0 mL of deionized water. To each sample cup were added 0.8 mL of sample or calibrator (containing unknown and known the antibody). and, therefore, the antibody affinity amounts of ferriting, respectively) and 0.5 mL of conjugate (monoclonal anti-ferritin-alkaline phosphatase conjugate Hybritech). After one hour of rocking on an Ames Rocker at room temperature, the assay was stopped by decanting. The sample cups were washed three times with 5.0 mL of deionized water 0.75 mL of Release Reagent A (1M DEA, 0.1 mM $MgCl_2$. pH 8.9) was added and incubated for 15 minutes at room temperature on an Ames Rocker. The enzyme activity in the release solution was measured in two ways, utilizing endpoint and rate measurements.

A 0.12-mL portion was removed and added to 0.75 mL of Release Redagent A containing 1 mM para-nitrophenylphosphate. This solution was incubated at 37° for 15 minutes and the reaction stopped by the addition of 0.75 mL of phosphate buffer (0.15M, pH 7.8). This stopped reaction was read at 405 nanometer (on a Hybritech Photon ERA Spectrophotometer) and the data presented in Table 2 below.

Another 0.5-mL portion of the release solution was removed and automatically injected into an aca ® analytical test pack (Lot #U60984) in the filling station of the instrument followed by a volume of buffer sufficient to bring the final in-pack volume to 5 mL. The pack was automatically processed at 37° with the addition of reagents required for the signal generating reaction at either breaker/mixer I or breaker/mixer II and the photometric readout of the signal was measured. These data are also shown in Table 2.

TABLE 2

| Ferritin Concentration (nanogram per mL) | Endpoint (mA at 405 nm) | Rate (mA/min at 405 nm) |
|---|---|---|
| 0 | 0.032 | −7.8 |
| 50 | 0.116 | −3.6 |
| 100 | 0.266 | −1.8 |
| 250 | 0.726 | +7.0 |
| 500 | 1.342 | 16.8 |

EXAMPLE 3

This example was identical to Example 2 except the release reagent also contained 1% BSA. The data are presented in Table 3.

TABLE 3

| Ferritin Concentration (ng/mL) | Endpoint (mA at 405 nm) | Rate (mA/min at 405 nm) |
|---|---|---|
| 0 | 0.41 | 0.6 |
| 50 | 0.22 | 0.6 |
| 100 | 0.44 | 10.2 |
| 250 | 1.16 | 29.4 |
| 500 | 2.10 | 61.8 |

EXAMPLE 4

Polystyrene tubes (Falcon, 12×75 mm) were coated with 0.2 mL of monoclonal antibody to anti-carcinoembryonic antigen (CEA) (Hybritech) diluted in phosphate buffered saline (Sigma Chemical P8033, 120 mM sodium chloride 2.7 mM potassium chloride and 10 mM phosphates) to a final concentration of 0.1 mg/mL. The tubes were rotated on a ferris wheel rotator for 30 minutes at room temperature. The antibody solution was decanted and the tubes were washed three times with 5.0 mL of deionized water. To each tube were added 0.8 mL of sample or calibrator and 0.4 mL of conjugate (monoclonal anti-CEA alkaline phosphatase conjugate) diluted 1/20 in a conjugate diluent (10% mannitol, 5% BSA, 50 mM TRIS, 0.15M NaCl, 0.3% chloroacetamide, 0.1 mM $MgCl_2$, 0.01 mM $ZnCl_2$, and 0.1% sodium azide pH 8.0). After rotating for one hour at room temperature, the reaction was stopped by decanting. The tubes were washed three times with 5.0 mL of deionized water 0.75 mL of Release Reagent A containing 0.5% Tween 20 (Sigma Chemicals P1320 polyoxyethylenesorbitan monolaurate) was added and mixed by rotating on the ferris wheel rotator for one hour at room temperature. The resulting release solution was analyzed for alkaline phosphatase activity using the Du Pont aca ® analyzer as described in Example 2. The data are presented below in Table 4.

TABLE 4

| Carcinoembryonic Antigen (nanogram per mL) | Rate (mA/min at 405 nm) |
|---|---|
| 0 | 4.2 |
| 5 | 9.8 |
| 10 | 19.5 |
| 50 | 103.2 |

I claim:

1. In a heterogeneous immunoassay of this invention comprising any standard heterogeneous immunoassay wherein the improvement comprises the modification of assay steps as follows:
   (a) absorbing a binding partner of the analyte of interest on a solid or liquid support to permit subsequent release of said binding partner from said support after the formation of a complex between the binding partner, said analyte; and a labeled binding partner;
   (b) storing said support having said binding partner absorbed thereon under conditions which preserve said releasability;
   (c) contacting said support having said binding partner absorbed thereon with said analyte and a labeled binding partner of the analyte to form a complex;
   (d) contacting the complex formed in step (c) with a release agent selected from the group consisting of monovalent salts, surfactants and organic bases; and
   (e) measuring the amount of label in said complex released in step (d) from said support.

2. The immunoassay of claim 1 wherein the release reagent is an amine.

3. The immunoassay of claim 1 wherein the support is a solid support.

4. The immunoassay of claim 1 wherein the support is a liquid support.

* * * * *